(12) United States Patent
Kurochi et al.

(10) Patent No.: US 8,890,079 B2
(45) Date of Patent: Nov. 18, 2014

(54) RADIATION DETECTION DEVICE AND RADIATION TOMOGRAPHIC APPARATUS, AND METHOD FOR ASSEMBLING RADIATION DETECTION DEVICE

(75) Inventors: Haruo Kurochi, Tokyo (JP); Abdelaziz Ikhlef, Waukesha, WI (US); Joseph James Lacey, Waukesha, WI (US); Richard P. Vandeweghe, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 326 days.

(21) Appl. No.: 13/537,621

(22) Filed: Jun. 29, 2012

(65) Prior Publication Data

US 2014/0001371 A1  Jan. 2, 2014

(51) Int. Cl.
*G21K 1/02* (2006.01)
*G01T 1/16* (2006.01)
*B23P 11/00* (2006.01)

(52) U.S. Cl.
CPC . *G21K 1/025* (2013.01); *G01T 1/16* (2013.01); *B23P 11/00* (2013.01)
USPC ........................................ 250/363.1; 378/147

(58) Field of Classification Search
USPC .............................. 250/363.1, 505.1; 378/147
See application file for complete search history.

(56) References Cited

U.S. PATENT DOCUMENTS

| | | | |
|---|---|---|---|
| 7,612,343 B2 | 11/2009 | Vickers | |
| 7,844,032 B2 | 11/2010 | Vermilyea et al. | |
| 7,916,839 B2 | 3/2011 | Halazonetis et al. | |
| 8,126,119 B2 | 2/2012 | Kurochi | |
| 8,139,717 B2 | 3/2012 | Harding et al. | |
| 2009/0225955 A1 | 9/2009 | Igarashi et al. | |
| 2011/0096895 A1 | 4/2011 | Kurochi | |
| 2012/0219107 A1* | 8/2012 | Kurochi et al. | 378/19 |
| 2013/0034200 A1* | 2/2013 | Hsieh et al. | 378/7 |

FOREIGN PATENT DOCUMENTS

JP    2012013421    1/2012

* cited by examiner

*Primary Examiner* — Mark R Gaworecki
(74) *Attorney, Agent, or Firm* — Armstrong Teasdale LLP (57) ABSTRACT

A radiation detection device is provided. The radiation detection device includes a pair of rails spaced in a slice direction and extending parallel to a channel direction, and a plurality of collimator modules arranged along the channel direction on a radiation exit side of the pair of rails, wherein at least one of the pair of rails extending along the channel direction includes a plate member with a plurality of notches formed along the radiation exit side, and wherein the collimator modules each include a first pin protruding on a radiation incidence side and attached to the pair of rails with the first pin fitted in one of the notches of the plate member.

20 Claims, 10 Drawing Sheets

RADIATION DETECTION DEVICE AND RADIATION TOMOGRAPHIC APPARATUS, AND METHOD FOR ASSEMBLING RADIATION DETECTION DEVICE

BACKGROUND OF THE INVENTION

The present invention relates to a radiation detection device with a collimator and a radiation tomographic apparatus with the radiation detection device, and a method for assembling the radiation detection device.

The radiation detection device provided in a radiation tomographic apparatus or the like includes a detection assembly which detects radioactive rays and a collimator assembly which removes scattered rays. The detection assembly has a structure that includes a plurality of detection elements is arranged in a matrix pattern. The collimator assembly has a structure that includes a plurality of collimator plates is arranged in a way to partition the detection elements on the detection plane of the detection assembly (see JP-A-2012-013421).

The performance of the radiation detection device largely depends on the positioning accuracy of the detection elements of the detection assembly and the collimator plates of the collimator assembly. Particularly, with the recent tendency toward multiple-array detection assemblies, the number of detection elements has increased and the collimator assembly size has become larger, so the importance of the accuracy in positioning them is growing.

However, as the detection assembly and the collimator assembly become larger in size, it is more difficult to improve the positioning accuracy. Specifically, it is difficult to position the collimator modules of the collimator assembly with high accuracy efficiently.

In the abovementioned circumstances, a technique for efficiently positioning the collimator modules in the radiation detection device with high accuracy is hoped for.

BRIEF DESCRIPTION OF THE INVENTION

In a first aspect, a radiation detection device is provided which includes a pair of rails spaced in a slice direction, extending parallel to a channel direction and a plurality of collimator modules arranged along the channel direction on a radiation exit side of the pair of rails. In the device, at least one of the pair of rails extends along the channel direction and has a plate member with a plurality of notches formed along the radiation exit side, and the collimator modules each have a first pin protruding on a radiation incidence side and are attached to the pair of rails with the first pin fitted in one of the notches of the plate member.

In a second aspect, in the radiation detection device according to the first aspect, the pair of rails each have the plate member and the collimator modules each have the first pins at both ends in the slice direction.

In a third aspect, in the radiation detection device according to the first or second aspect, the notches are each formed at every reference position for arrangement of the collimator modules.

In a fourth, in the radiation detection device according to any one of the first to third aspects, at least one of the pair of rails has the plate member and a flat surface formed at a reference position for the collimator modules in the slice direction and a lateral side of the first pin abuts on the flat surface.

In a fifth aspect, the radiation detection device according to any one of the first to fourth aspects further includes a plurality of detector modules provided on a radiation exit side of the collimator modules. The collimator modules each have a second pin protruding on the radiation exit side and the detector modules each have a hole to fit the second pin and are attached to the pair of rails with the second pin fitted in the hole.

In a sixth aspect, in the radiation detection device according to the fifth aspect, the second pin is formed integrally with the first pin.

In a seventh aspect, in the radiation detection device according to the fifth aspect, the collimator modules each have the second pins at both ends in the slice direction and the detector modules each have the holes at both ends in the slice direction.

In an eighth aspect, the radiation detection device according to any one of the first to fourth aspects further includes a plurality of detector modules provided on a radiation exit side of the collimator modules. The detector modules each have a second pin protruding on the radiation incidence side, the collimator modules each have a hole to fit the second pin, and the detector modules are attached to the pair of rails with the second pin fitted in the hole.

In a ninth aspect, in the radiation detection device according to the eighth aspect, the detector modules each have the second pins at both ends in the slice direction and the collimator modules each have the holes at both ends in the slice direction.

In a tenth aspect, a radiation tomographic apparatus is provided which has a radiation detection device which includes a pair of rails spaced in a slice direction, extending parallel to a channel direction and a plurality of collimator modules arranged along the channel direction on a radiation exit side of the pair of rails. At least one of the pair of rails extends along the channel direction and has a plate member with a plurality of notches formed along the radiation exit side. The collimator modules each have a first pin protruding on a radiation incidence side and are attached to the pair of rails with the first pin fitted in one of the notches of the plate member.

In an eleventh aspect, in the radiation tomographic apparatus according to the tenth aspect, the pair of rails each have the plate member and the collimator modules each have the first pins at both ends in the slice direction.

In a twelfth aspect, in the radiation tomographic apparatus according to the tenth or eleventh aspect, the notches are each formed at every reference position for arrangement of the collimator modules.

In a thirteenth aspect, in the radiation tomographic apparatus according to any one of the tenth to twelfth aspects, at least one of the pair of rails has the plate member and a flat surface formed at a reference position for the collimator modules in the slice direction and a lateral side of the first pin abuts on the flat surface.

In a fourteenth aspect, the radiation tomographic apparatus according to any one of the tenth to thirteenth aspects further includes a plurality of detector modules provided on a radiation exit side of the collimator modules. The collimator modules each have a second pin protruding on the radiation exit side and the detector modules each have a hole to fit the second pin and are attached to the pair of rails with the second pin fitted in the hole.

In a fifteenth aspect, in the radiation tomographic apparatus according to the fourteenth aspect, the second pin is formed integrally with the first pin.

In a sixteenth aspect, in the radiation tomographic apparatus according to the fourteenth aspect, the collimator modules each have the second pins at both ends in the slice direction and the detector modules each have the holes at both ends in the slice direction.

In a seventeenth aspect, the radiation tomographic apparatus according to any one of the tenth to thirteenth aspects further includes a plurality of detector modules provided on a radiation exit side of the collimator modules. The detector modules each have a second pin protruding on the radiation incidence side and the collimator modules each have a hole to fit the second pin, and the detector modules are attached to the pair of rails with the second pin fitted in the hole.

In an eighteenth aspect, in the radiation tomographic apparatus according to the seventeenth aspect, the detector modules each have the second pins at both ends in the slice direction and the collimator modules each have the holes at both ends in the slice direction.

In a nineteenth aspect, a method for assembling a radiation detection device is provided which includes the steps of fixing a plate member extending in a channel direction and having a plurality of notches formed along a radiation exit side along the channel direction on at least one of a pair of rails spaced in a slice direction, extending parallel to the channel direction, and attaching a plurality of collimator modules to the pair of rails while first pins provided on a radiation incidence side of the collimator modules are fitted in the notches of the plate member.

In a twentieth aspect, the method for assembling a radiation detection device according to the nineteenth aspect further includes the step of attaching a plurality of detector modules to the pair of rails while second pins provided on a radiation exit side of the collimator modules are fitted in holes formed on a radiation incidence side of the detector modules.

According to the above aspects, considering that the collimator modules must be positioned with high accuracy but usually it is difficult to position them in the channel direction with high accuracy, plate members as components have notches to fit the positioning pins of the collimator modules instead of any means provided in the rails for high accuracy positioning in the channel direction. The plate members are manufactured with high precision in advance and they are attached to the rails so that a standard procedure for high accuracy positioning is established relatively easily. Therefore, a rail which provides high positioning accuracy can be assembled with a high yield rate. Positioning of the collimator modules can be easily done simply by fitting the positioning pins into the notches of the plate members. As a result, the collimator modules of the radiation detection device can be positioned with high accuracy efficiently.

DETAILED DESCRIPTION OF THE INVENTION

Exemplary embodiments are described herein.

Figure 1:
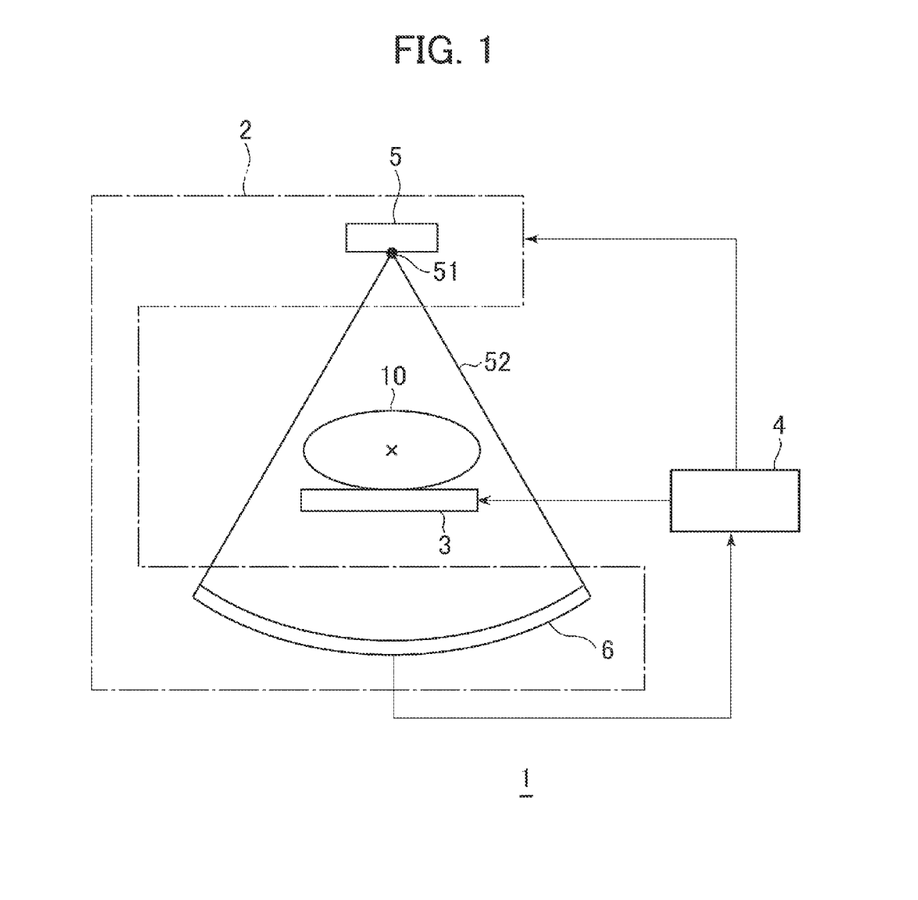
FIG. 1 is a schematic view showing the configuration of an exemplary X-ray CT apparatus.

FIG. 1 schematically shows the configuration of an exemplary X-ray CT (Computed Tomography) apparatus 1. As shown in FIG. 1, the X-ray CT apparatus 1 includes a scanning gantry 2, an imaging table 3, and an operation console 4.

Under the control of the operation console 4, the scanning gantry 2 scans a subject 10 and collects projection data. The imaging table 3 holds the subject 10 on it and transports it into the bore of the scanning gantry 2. Upon receipt of an operation command from an operator, the operation console 4 controls the scanning gantry 4 and imaging table 3 or reconstructs an image based on the projection data collected by scanning and displays it.

The scanning gantry 2 has an X-ray tube 5 and an X-ray detection device 6. The X-ray tube 5 and X-ray detection device 6 are located opposite to each other with the subject 10 between them and supported in a way to rotate around the subject 10 while this positional relation is maintained. The X-ray tube 5 radiates X rays 52 from its X-ray focal point 51 toward the subject 10 and the X-ray detection device 6 detects the transmitted X rays.

Next, the structure of the X-ray detection device 6 will be described.

Figure 2:
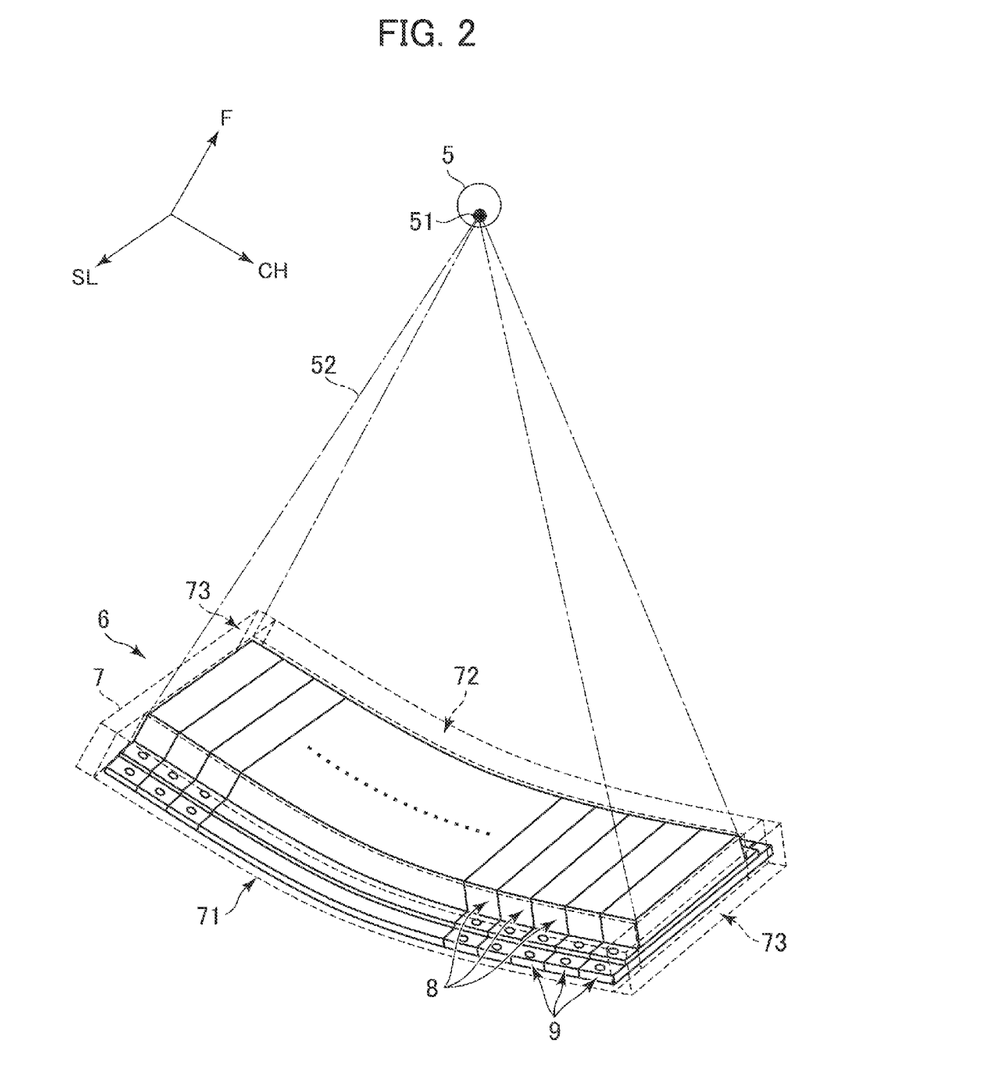
FIG. 2 is a view showing the structure of an exemplary X-ray detection device.

FIG. 2 is a perspective view schematically illustrating the structure of the X-ray detection device 6. As shown in FIG. 2, the X-ray detection device 6 includes a frame 7, a plurality of collimator modules 8, and a plurality of detector modules 9.

The frame 7 includes a pair of rails spaced in a slice direction (SL direction), extending parallel to a channel direction (CH direction), namely a top rail 71 and a bottom rail 72, and connections 73 connecting this pair of rails at both ends in the channel direction. Here, "top" means one directional side in the slice direction and "bottom" means the other directional side in the slice direction, namely the side opposite to the top. The top and bottom rails 71 and 72 and the connections 73 are, for example, made of stainless alloy or aluminum alloy.

Figure 3:
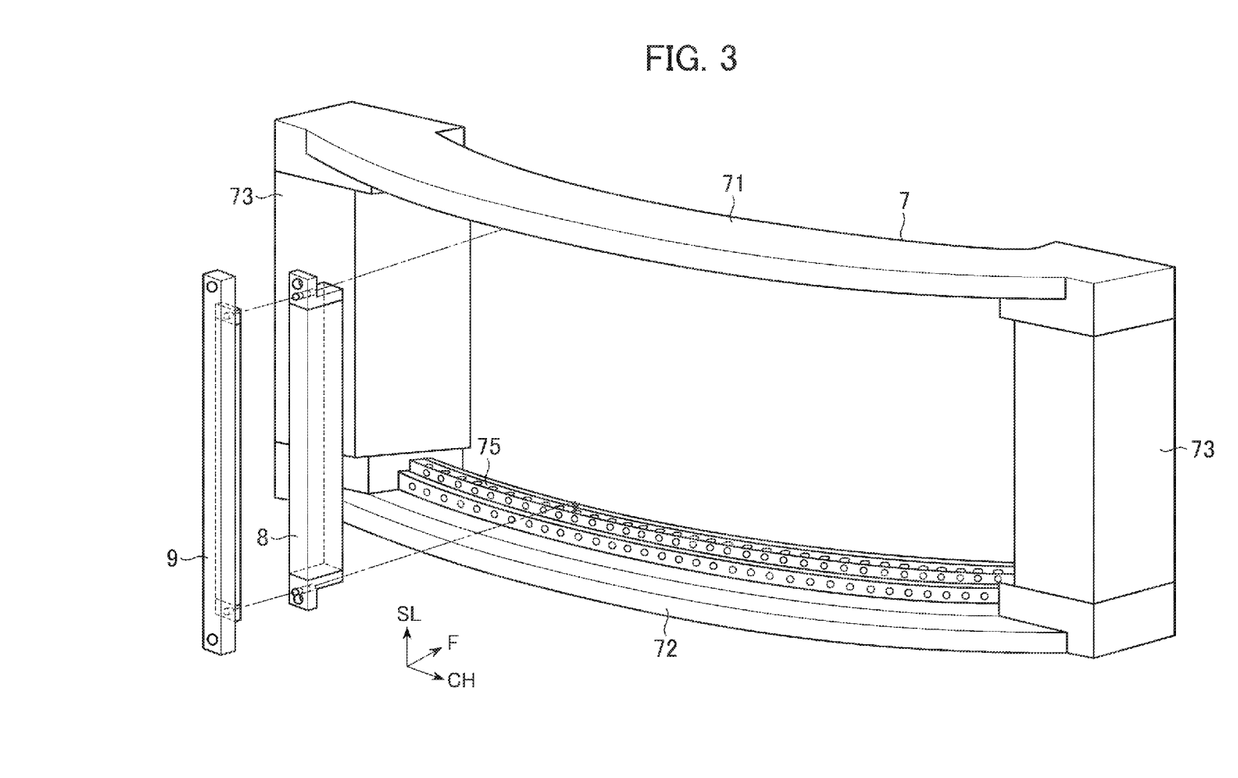
FIG. 3 is a perspective view of the X-ray detection device shown in FIG. 2.
Figure 4:
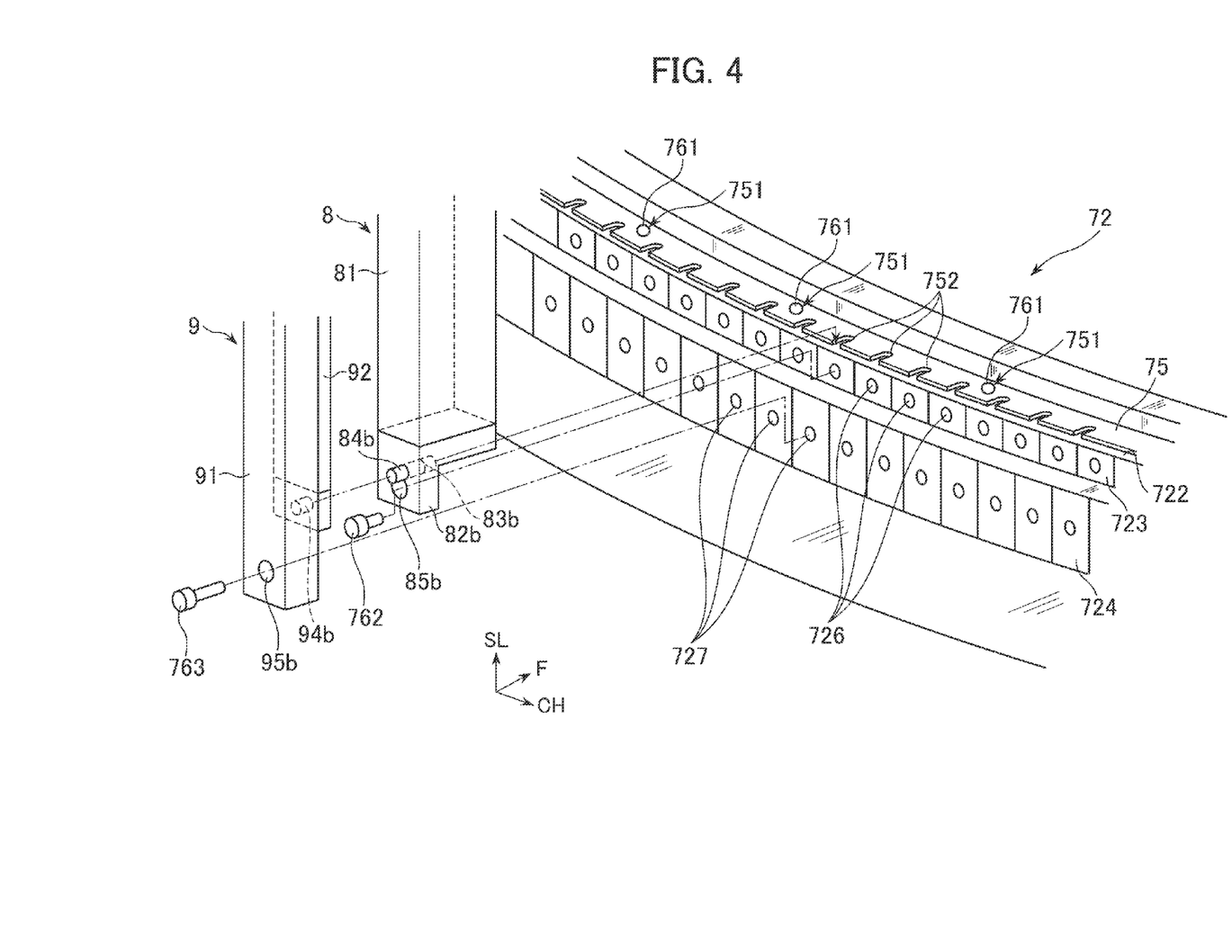
FIG. 4 is a fragmentary enlarged view of the X-ray detection device shown in FIG. 2.
Figure 5:
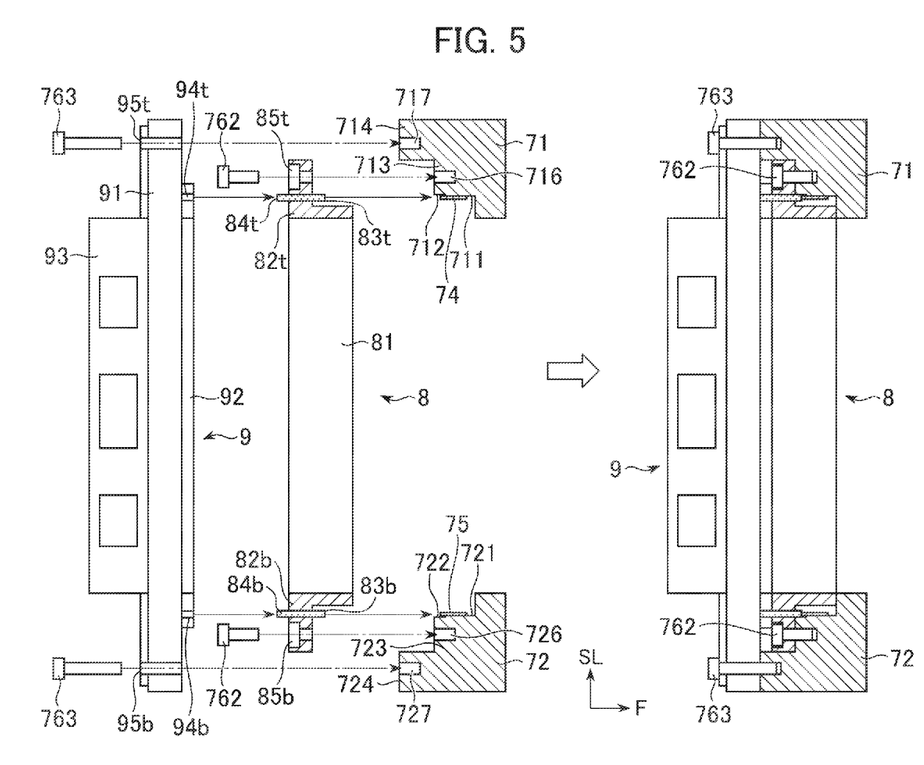
FIG. 5 is a sectional view of the X-ray detection device shown in FIG. 2.

FIG. 3 is a perspective view showing an example of the structure of the X-ray detection device 6, as seen from the X-ray exit side of the X-ray detection device 6. FIG. 4 is a fragmentary enlarged view of the X-ray detection device 6 shown in FIG. 3. FIG. 5 is a sectional view of the X-ray detection device 6, as taken perpendicularly to the channel direction.

As shown in FIGS. 4 and 5, a first flat surface 721 and a second flat surface 722 which are parallel to the X-ray radiation direction (F direction) and extend in the channel direction are formed as uneven parallel planes on the top side surface of the bottom rail 72. Also, a first curved surface 723 and a second curved surface 724 which are perpendicular to the X-ray radiation direction and extend in the channel direction are formed as uneven parallel planes on the X-ray exit side of the bottom rail 72.

A bottom positioning plate 75 is positioned accurately and fixed on the first flat surface 721 of the bottom rail 72. The bottom positioning plate 75 is intended to position the collimator modules 8 in the channel direction. As shown in FIG. 4, in this example, the bottom positioning plate 75 is fixed by aligning a plurality of mounting holes 751 in the bottom positioning plate 75 to a plurality of positioning plate mounting holes 725 (not shown) in the first flat surface 721 of the bottom rail 72 and inserting positioning plate mounting pins 761 into the holes, in each of which a positioning plate mounting hole 725 and a mounting hole 751 overlap.

The bottom positioning plate 75 is an arch-like flat plate member extending in the channel direction. On the X-ray exit side of the bottom positioning plate 75, a plurality of notches 752 are each provided at every reference position for arrangement of the collimator modules 8 and spaced in the channel direction. In other words, the spacing between notches 752 is the same as the required spacing between collimator modules 8. The bottom positioning plate 75 is, for example, made of stainless alloy or aluminum alloy. The notches 752 are intended to position the collimator modules 8 accurately in the channel direction and machined with high precision by a wire electric discharge process or the like.

The second flat surface 722 of the bottom rail 72 is a reference plane for positioning the collimator modules 8 in the slice direction accurately. For this reason, the first flat surface 721 of the bottom rail 72 is machined with high precision so as to be in a prescribed positional relationship with the standard position of the X-ray detection device 6. In this example, the second flat surface 722 is slightly lower or nearer to the bottom side than the first flat surface 721 and partly overlaps the notches 752 in the slice direction.

On the first curved surface 723 of the bottom rail 72, a plurality of collimator module mounting screw holes 726 for fixing the collimator modules 8 with collimator module mounting screws 762 are formed and spaced in the channel direction.

On the second curved surface 724 of the bottom rail 72, a plurality of detector module mounting screw holes 727 for fixing the detector modules 9 with detector module mounting screws 763 are formed and spaced in the channel direction.

The top rail 71 has a structure which is almost symmetrical with the bottom rail 72 in the slice direction. Specifically, a first flat surface 711 is formed on the bottom side surface of the top rail 71 and a first curved surface 713 and a second curved surface 714 are formed as uneven parallel planes on the X-ray exit side of the top rail 71.

Like the bottom positioning plate 75, a top positioning plate 74 is positioned and fixed accurately on the first flat surface 711 of the top rail 71. On the X-ray exit side of the top positioning plate 74, a plurality of notches 742 (not shown) are each provided at every reference position for arrangement of the collimator modules 8 and spaced in the channel direction. The notches 742 are intended to position the collimator modules 8 accurately in the channel direction and machined with high precision by a wire electric discharge process or the like.

The second flat surface 712 of the top rail 71 is a plane for roughly positioning the collimator modules 8 in the slice direction. Since the second flat surface 712 of the top rail 71 is not a reference plane for positioning, it need not be actually machined with so high precision as the second flat surface 722 of the bottom rail 72, though the machining precision need not be different between them. In this example, the second flat surface 712 is slightly higher or nearer to the top side than the first flat surface 711 and partially overlaps notches 742 in the slice direction.

On the first curved surface 713 of the top rail 71, a plurality of collimator module mounting screw holes 716 for fixing the collimator modules 8 with collimator module mounting screws 762 are formed and spaced in the channel direction. Also, on the second curved surface 714 of the top rail 71, a plurality of detector module mounting screw holes 717 for fixing the detector modules 9 with detector module mounting screws 763 are formed and spaced in the channel direction.

Figure 6:
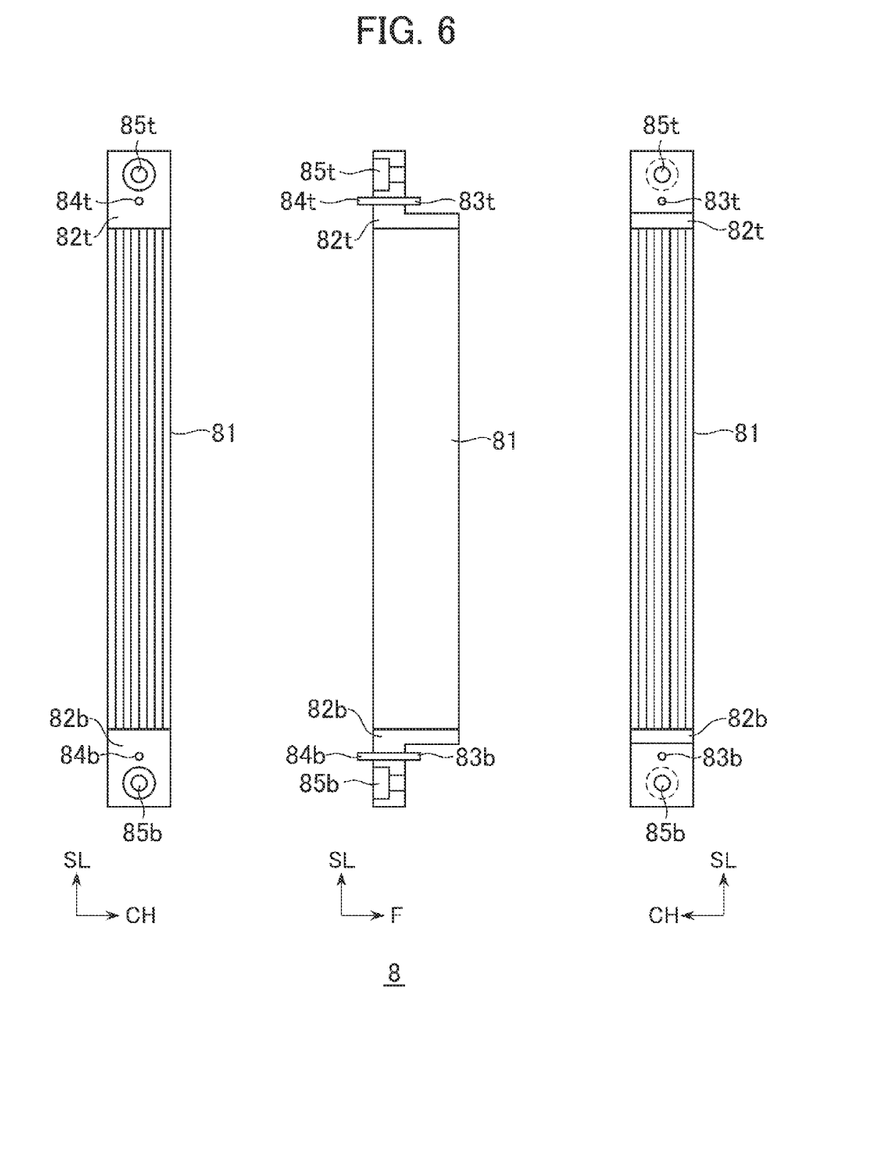
FIG. 6 shows the structure of an exemplary collimator module.

Next, the structure of a collimator module 8 will be described. FIG. 6 shows an exemplary collimator module structure.

As shown in FIG. 6, the collimator module 8 includes a plurality of collimator plates 81 combined in a grid pattern so as to correspond to boundaries between detection elements 91 of the detector module 9, and a pair of end-blocks, namely a top end-block 82$t$ and a bottom end-block 82$b$ which support the collimator plates 81 by sandwiching them in the slice direction. The collimator plates 81 are, for example, made of a heavy metal which absorbs X rays, such as tungsten or molybdenum. The top and bottom end-blocks 82$t$ and 82$b$ are, for example, made of aluminum alloy. The collimator plates 81 and top and bottom end-blocks 82$t$ and 82$b$ are positioned with a prescribed tool and fixed with an adhesive agent. The collimator plates 81 are combined, for example, in a way to produce 64 segments (in the slice direction) by 16 segments (in the channel direction), in which each segment is about 1 mm square.

The collimator module 8 has, on the X-ray incidence side at both ends in the slice direction, a top collimator module positioning pin 83$t$ and a bottom collimator module positioning pin 83$b$ respectively in order to position the module itself. In this example, the top collimator module positioning pin 83$t$ is located in the center of the top end-block 82$t$ in the channel direction and the bottom collimator module positioning pin 83$b$ is located in the center of the bottom end-block 82$b$ in the channel direction. The top collimator module positioning pin 83$t$ and the bottom collimator module positioning pin 83$b$ are cylindrical members protruding on the X-ray incidence side which are formed so as to fit the notches 742 of the top positioning plate 74 and the notches 752 of the bottom positioning plate 75 exactly. In other words, the diameter of the top and bottom collimator module positioning pins 83$t$ and 83$b$ is almost the same as the width of the top and bottom notches 742 and 752 in the channel direction.

The collimator module 8 is accurately positioned in the channel direction by fitting its top collimator module positioning pin 83$t$ into a notch 742 of the top positioning plate 74 and fitting its bottom collimator module positioning pin 83$b$ into a notch 752 of the bottom positioning plate 75. The collimator module 8 is accurately positioned in the slice direction by letting the bottom collimator module positioning pins 83$b$ abut on the first flat surface 721 of the bottom rail 72.

The collimator module 8 has a top fixing hole 85$t$ and a bottom fixing hole 85$b$ formed at both ends in the slice direction respectively. The top fixing hole 85$t$ is a hole in which the collimator module mounting screw 762 is passed in order to screw the collimator module 8 in the collimator module mounting screw hole 716 of the top rail 71. The bottom fixing hole 85$b$ is a hole in which the collimator module mounting screw 762 is passed in order to screw the collimator module 8 in the collimator module mounting screw hole 726 of the bottom rail 72.

The collimator module 8 further has a top detector module positioning pin 84$t$ and a bottom detector module positioning pin 84$b$ for positioning the detector module 9, on the X-ray exit side at both ends in the slice direction, namely opposite to the side where the top and bottom collimator module positioning pins 83$t$ and 83$b$ are located. In the exemplary embodiment, the top detector module positioning pin 84$t$ is located in the center of the top end-block 82$t$ in the channel direction and the bottom detector module positioning pin 84$b$ is located in the center of the bottom end-block 82$b$ in the channel direction. The top and bottom detector module positioning pins 84$t$ and 84$b$ are cylindrical members protruding on the X-ray exit side which are formed so as to accurately fit the top and bottom positioning holes (described later) formed on the X-ray incidence side at both ends of the detector module 9 in the slice direction.

The detector module 9 is accurately positioned in the channel and slice directions by fitting the top and bottom detector module positioning pins 84t and 84b in the top and bottom positioning holes of the detector module 9 respectively with the collimator module 8 attached to a pair of rails 71 and 72.

In the exemplary embodiment, the top collimator module positioning pin 83t and the top detector module positioning pin 84t are formed integrally with each other. Similarly, the bottom collimator module positioning pin 83b and the bottom detector module positioning pin 84b are formed integrally with each other. Specifically, through-holes are made in the top and bottom end-blocks 82t and 82b in the X-ray radiation direction and a pin is inserted into each through-hole and fixed. This stabilizes the positional accuracy of the positioning pins and improves the assembling efficiency.

Figure 7:
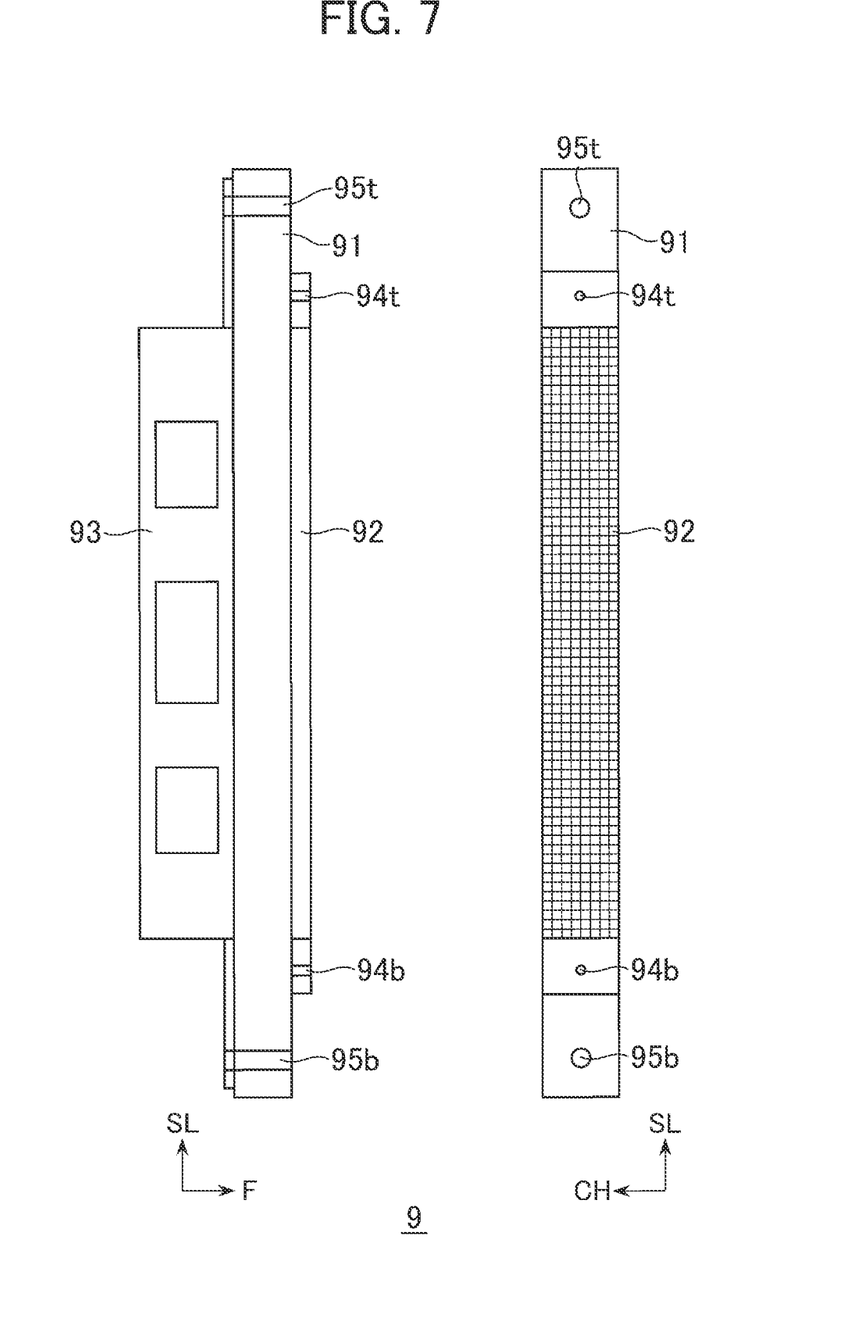
FIG. 7 shows the structure of an exemplary detector module.

Next, the structure of the detector module 9 will be described. FIG. 7 shows an exemplary detector module structure.

As shown in FIG. 7, the detector module 9 includes a substrate 91, a plurality of detection elements 92 arranged in a matrix pattern on the X-ray incidence side of the substrate 91, and a signal processing circuit 93 which is located on the X-ray exit side of the substrate 91 and converts analog output signals from the detection elements 92 into digital signals and process them. The substrate 91 is, for example, made of ceramics. The detection elements 92 are each comprised of a scintillator and a photo-diode. Each detection element 92 is, for example, about 1 mm square and in one detector module 9, for example, 64 (in the slice direction) by 16 (in the channel direction) detection elements 92 are arranged.

The detector module 9 has, on the X-ray incidence side at both ends in the slice direction, a top positioning hole 94t and a bottom positioning hole 94b respectively in order to position the module itself. The top and bottom positioning holes 94t and 94b are so formed as to fit the top and bottom detector module positioning pins 84t and 84b of the collimator module 8 respectively.

The detector module 9 has a top fixing hole 95t and a bottom fixing hole 95b formed at both ends in the slice direction respectively. The top fixing hole 95t is a hole in which the detector module mounting screw 763 is passed in order to screw the detector module 9 in the detector module mounting screw hole 717 of the top rail 71. The bottom fixing hole 95b is a hole in which the detector module mounting screw 763 is passed in order to screw the detector module 9 in the detector module mounting screw hole 727 of the bottom rail 72.

Next, the method for assembling the X-ray detection device will be described.

Figure 8:
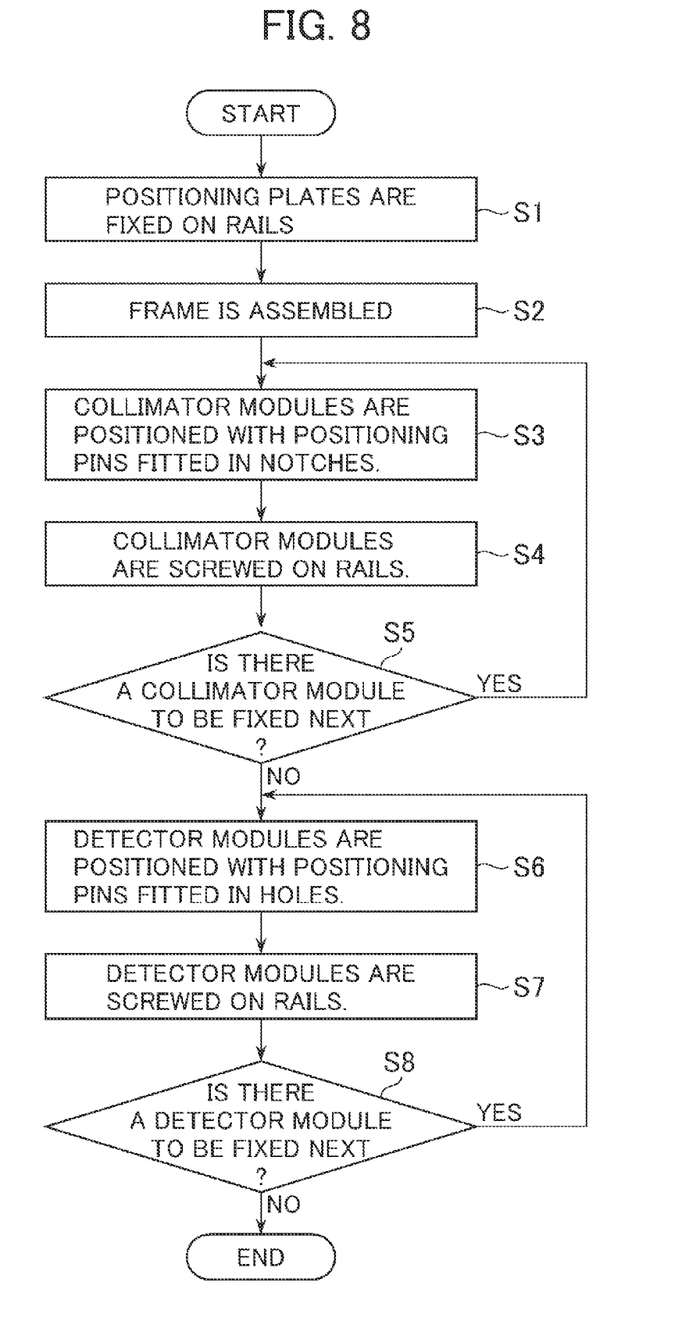
FIG. 8 is a flowchart of an exemplary method for assembling an X-ray detection device.

FIG. 8 is a flowchart of an exemplary method for assembling the X-ray detection device.

At Step S1, the positioning plates are fixed on the rails. Specifically, the following procedure is taken. The top positioning plate 74 is placed on the first flat surface 711 of the top rail 71. The position of the top positioning plate 74 is adjusted so that the mounting holes 741 of the top positioning plate 74 overlap the positioning plate mounting holes 715 of the top rail 71. The positioning plate mounting pins 761 are driven into the respective mounting holes 741 to fix the top positioning plate 74 on the first flat surface 711 of the top rail 71. A similar procedure is taken for the bottom rail 72. Specifically, the bottom positioning plate 75 is fixed on the first flat surface 721 of the bottom rail 72 by making the mounting holes 751 of the bottom positioning plate overlap the positioning plate mounting holes 725 of the bottom rail 71 and driving the positioning plate mounting pins 761 into the holes.

At Step S2, the top and bottom rails 71 and 72 positioned at Step S1 are connected using the connections 73 to assemble the frame 7.

At Step S3, the collimator modules are positioned by the positioning pins. Specifically, the following procedure is taken. The top and bottom collimator module positioning pins 83t and 83b of each collimator module 8 are fitted into the notches 742 and 752 of the corresponding pair of top and bottom positioning plates 74 and 75 respectively. Consequently the collimator module 8 is positioned accurately in the channel direction. At this time, the bottom collimator module positioning pin 83b is pressed against the second flat surface 722 of the bottom rail 72. Consequently the collimator module 8 is accurately positioned in the slice direction.

At Step S4, the collimator modules are fixed on the rails with screws. Specifically, the following procedure is taken. With each collimator module 8 positioned in place, the collimator module mounting screws 762 are passed into the collimator module mounting screw hole 716 of the top rail 71 and the collimator module mounting screw hole 726 of the bottom rail 72 to screw the collimator module 8.

At Step S5, a decision is made as to whether there is a collimator module 8 to be fixed next. If so, the sequence goes back to Step S3 and the fixing procedure for the collimator modules 8 is continued. If not, the sequence proceeds to Step S6.

At Step S6, the detector modules are positioned by the positioning pins. Specifically, the following procedure is taken. The top and bottom detector module positioning pins 84t and 84b of each collimator module 8 attached to the pair of rails 71 and 72 are fitted into the top and bottom positioning holes 94t and 94b of a detector module 9. Consequently the detector module 9 is positioned in both the channel direction and slice direction at a time. As a result, the boundaries of the detection elements 92 of the detector module 9 exactly correspond to the grid pattern of the collimator plates 81 of the collimator module 8 in terms of position.

At Step S7, the detector modules are fixed on the rails with screws. Specifically, the following procedure is taken. With each detector module 9 positioned in place, the detector module mounting screws 763 are passed into the detector module mounting screw hole 717 of the top rail 71 and the detector module mounting screw hole 727 of the bottom rail 72 to screw the detector module 9.

At Step S8, a decision is made as to whether there is a detector module 9 to be fixed next. If so, the sequence goes back to Step S6 and the fixing procedure for the detector modules is continued. If not, the assembling sequence is finished.

According to the above embodiment, considering that the collimator modules must be positioned with high accuracy but usually it is difficult to position them in the channel direction with high accuracy, positioning plates as components have notches to fit the positioning pins of the collimator modules instead of any means provided in the rails for high accuracy positioning in the channel direction. The positioning plates are manufactured with high precision in advance and they are attached to the rails so that a standard procedure for high accuracy positioning is established relatively easily. Therefore, a rail which provides high positioning accuracy can be assembled with a high yield rate. Positioning of the collimator modules can be easily done simply by fitting the positioning pins into the notches of the positioning plates. As a result, the collimator modules of the radiation detection device can be positioned with high accuracy efficiently.

In this embodiment, since the positioning and fixing procedures for each collimator module are similar to those for each individual detector module, the X-ray detection device can be assembled by carrying out simple steps repeatedly, so working efficiency and high maintainability are ensured.

Furthermore, in this embodiment, detector modules, which are sensitive to temperature, are directly fixed on the rails, so heat transfer is done efficiently and the characteristics of the detector modules are stabilized.

In addition, since the collimator modules correspond to the detector modules in the channel direction in terms of position, the number of detection elements of the X-ray detection device in the channel direction, or the width of the detecting surface in the channel direction, can be easily increased or decreased.

The above embodiment is merely exemplary, and the systems and methods described herein may be embodied in any modified form without departing from the spirit and scope of the invention.

Figure 9:
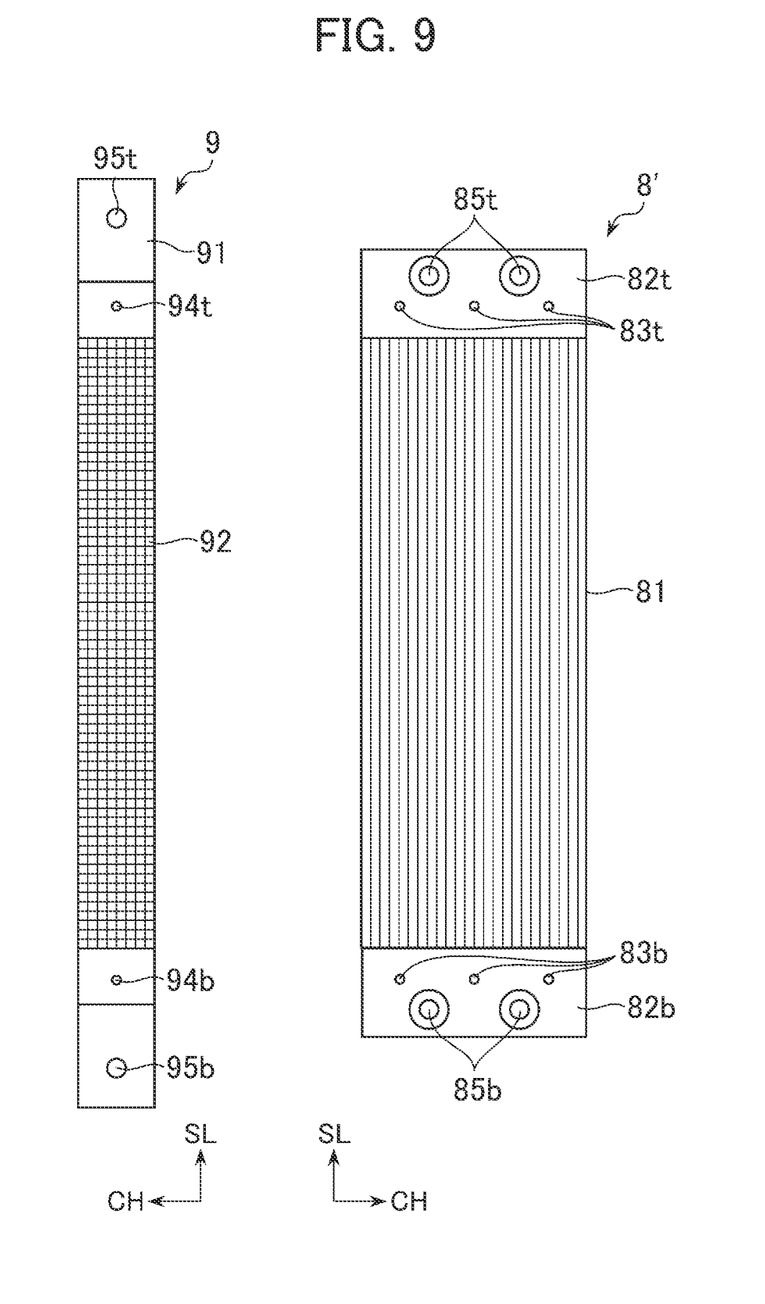
FIG. 9 shows an alternative embodiment of the collimator module and detector module.

For example, in the exemplary embodiment, one detector module is positioned for one collimator module; however, as shown in FIG. 9, a plurality of detector modules may be positioned for one collimator module.

Figure 10:
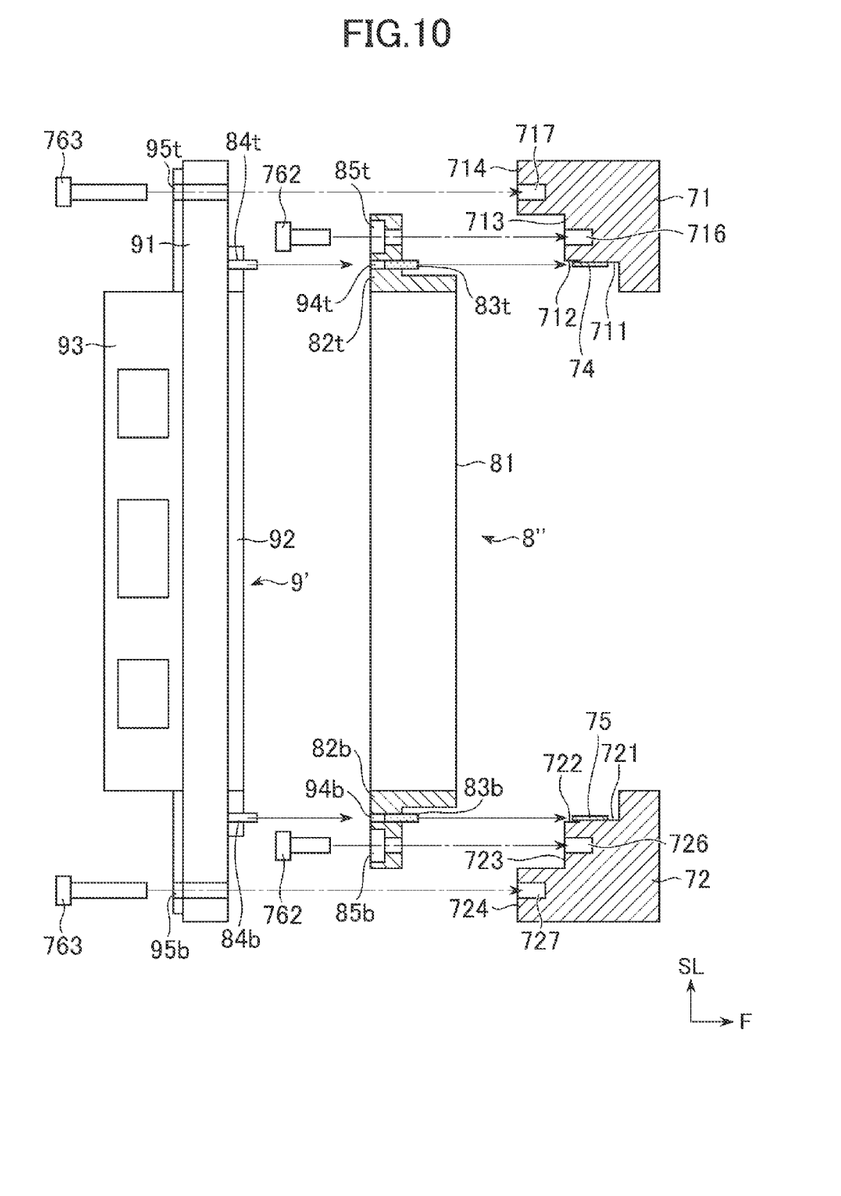
FIG. 10 shows another alternative embodiment of the collimator module and detector module.

Furthermore, for example, in the exemplary embodiment, each collimator module has positioning pins for a detector module and the detector module has positioning holes in which the positioning pins are fitted; however, as shown in FIG. 10, the locations of the positioning pins and positioning holes may be reversed. Namely, the collimator module may have detector module positioning holes and the detector module may have positioning pins.

Furthermore, for example, in the exemplary embodiment, the collimator modules and detector modules have positioning pins and positioning holes at both ends in the slice direction; however, a positioning pin and a positioning hole may be provided at only one end in the slice direction.

Furthermore, notches may be made in place of the collimator module mounting holes and detector module mounting holes.

Furthermore, the exemplary embodiment concerns an X-ray CT apparatus, but the methods and systems described herein may be applied to PET-CT equipment which combines an X-ray CT apparatus and a PET or SPECT-CT equipment which combines an X-ray CT apparatus and a SPECT.

Furthermore, in the exemplary embodiment, X rays are used for scanning but other radioactive rays such as gamma rays may be used.

What is claimed is:

1. A radiation detection device comprising:
a pair of rails spaced in a slice direction and extending parallel to a channel direction; and
a plurality of collimator modules arranged along the channel direction on a radiation exit side of the pair of rails, wherein at least one of the pair of rails extending along the channel direction comprises a plate member with a plurality of notches formed along the radiation exit side, and wherein the collimator modules each comprise a first pin protruding on a radiation incidence side and attached to the pair of rails with the first pin fitted in one of the notches of the plate member.

2. The radiation detection device according to claim 1, wherein each of the pair of rails comprise the plate member, and wherein the collimator modules each comprise the first pins at both ends in the slice direction.

3. The radiation detection device according to claim 1, wherein the notches are formed at each of a plurality of reference positions for arrangement of the collimator modules.

4. The radiation detection device according to claim 1, wherein at least one of the pair of rails comprises the plate member and a flat surface formed at a reference position for the collimator modules in the slice; direction, and wherein a lateral side of the first pin abuts on the flat surface.

5. The radiation detection device according to claim 1, further comprising:
a plurality of detector modules provided on a radiation exit side of the collimator modules, wherein the collimator modules each comprise a second pin protruding on the radiation exit side, and wherein the detector modules each comprise a hole to fit the second pin and are attached to the pair of rails with the second pin fitted in the hole.

6. The radiation detection device according to claim 5, wherein the second pin is formed integrally with the first pin.

7. The radiation detection device according to claim 5, wherein the collimator modules each comprise the second pins at both ends in the slice direction, and wherein the detector modules each comprise the holes at both ends in the slice direction.

8. The radiation detection device according to claim 1, further comprising:
a plurality of detector modules provided on a radiation exit side of the collimator modules, wherein the detector modules each comprise a second pin protruding on the radiation incidence side, wherein the collimator modules each comprise a hole to fit the second pin, and wherein the detector modules are attached to the pair of rails with the second pin fitted in the hole.

9. The radiation detection device according to claim 8, wherein the detector modules each comprise the second pins at both ends in the slice direction, and wherein the collimator modules each comprise the holes at both ends in the slice direction.

10. A radiation tomographic apparatus comprising a radiation detection device including:
a pair of rails spaced in a slice direction and extending parallel to a channel direction; and
a plurality of collimator modules arranged along the channel direction on a radiation exit side of the pair of rails, wherein at least one of the pair of rails extending along the channel direction comprises a plate member with a plurality of notches formed along the radiation exit side, and wherein the collimator modules each comprise a first pin protruding on a radiation incidence side and attached to the pair of rails with the first pin fitted in one of the notches of the plate member.

11. The radiation tomographic apparatus according to claim 10, wherein each of the pair of rails comprise the plate member, and wherein the collimator modules each comprise the first pins at both ends in the slice direction.

12. The radiation detection device according to claim 10, wherein the notches are formed at each of a plurality of reference positions for arrangement of the collimator modules.

13. The radiation tomographic apparatus according to claim 10, wherein at least one of the pair of rails comprises the plate member and a flat surface formed at a reference position for the collimator modules in the slice direction, and wherein a lateral side of the first pin abuts on the flat surface.

14. The radiation tomographic apparatus according to claim 10, further comprising:

a plurality of detector modules provided on a radiation exit side of the collimator modules, wherein the collimator modules each comprise a second pin protruding on the radiation exit side, and wherein the detector modules each comprise a hole to fit the second pin and are attached to the pair of rails with the second pin fitted in the hole.

15. The radiation tomographic apparatus according to claim 14, wherein the second pin is formed integrally with the first pin.

16. The radiation tomographic apparatus according to claim 14, wherein the collimator modules each comprise the second pins at both ends in the slice direction, and wherein the detector modules each comprise the holes at both ends in the slice direction.

17. The radiation tomographic apparatus according to claim 10, further comprising:
a plurality of detector modules provided on a radiation exit side of the collimator modules, wherein the detector modules each comprise a second pin protruding on the radiation incidence side, wherein the collimator modules each comprise a hole to fit the second pin, and wherein the detector modules are attached to the pair of rails with the second pin fitted in the hole.

18. The radiation tomographic apparatus according to claim 17, wherein the detector modules each comprise the second pins at both ends in the slice direction, and wherein the collimator modules each comprise the holes at both ends in the slice direction.

19. A method for assembling a radiation detection device comprising:
fixing a plate member extending in a channel direction and having a plurality of notches formed along a radiation exit side along the channel direction on at least one of a pair of rails spaced in a slice direction and extending parallel to the channel direction; and
attaching a plurality of collimator modules to the pair of rails such that first pins provided on a radiation incidence side of the collimator modules are fitted in the notches of the plate member.

20. The method for assembling a radiation detection device according to claim 19, further comprising the step of:
attaching a plurality of detector modules to the pair of rails such that second pins provided on a radiation exit side of the collimator modules are fitted in holes formed on a radiation incidence side of the detector modules.

* * * * *